(12) United States Patent
Arand et al.

(10) Patent No.: US 6,511,674 B1
(45) Date of Patent: *Jan. 28, 2003

(54) GARLIC COMPOSITION FOR FOLIAR APPLICATIONS

(76) Inventors: Anthony Arand, 219 Rancho Bonito Rd., Fallbrook, CA (US) 92028; John K. Arand, 5731 Mistridge Dr., Rancho Palos Verdes, CA (US) 90275

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 5 days.

(21) Appl. No.: 09/099,480

(22) Filed: Jun. 17, 1998

(51) Int. Cl.⁷ .................................................. A01N 25/32
(52) U.S. Cl. .................. 424/406; 424/405; 424/754; 504/101; 504/116
(58) Field of Search .............................. 424/195.1, 405, 424/406, 754; 504/101, 116

(56) References Cited

U.S. PATENT DOCUMENTS

| 5,429,817 A | * | 7/1995 | McKenzie | 424/195.1 |
| 5,711,953 A | * | 1/1998 | Bassett | 424/405 |
| 5,733,552 A | * | 3/1998 | Anderson et al. | 424/195.1 |

FOREIGN PATENT DOCUMENTS

| CN | 1116049 | * | 2/1996 |
| JP | 06056617 | * | 3/1994 |
| JP | 09/32570 | * | 5/1997 |
| JP | 10025217 | * | 1/1998 |

OTHER PUBLICATIONS

Bianchi et al Plant Disease vol. 81,#11 11/97 pp 1241–1246.*
Maoon et al (ROPProtection 3/97 vol. 16 #2 pp 107–108.*
Jood et al J. of AG. & Food Chem. vol. 41#10 pp 1644–1648 10/93.*
Nasseh—Zeit chrit for Angew andte enbtomologic vol. 95 #3 pp 228–230 4/83.*
Nasseh—Zeitchriff fun Angew Andte Entomologic vol. 92 #5 pp 464–471 12/81.*
Blacow ed. Martindale The EXTRA Pharmacopoeia p 710 '72.*
Garlic King Advertisement, Letter by Kevin Busenlehner, Jan. 9, 1995 (12 pages).
Cotton Farming 1/96.
"Garlic Wonderful Odor For This", Cline, California–Arizona Farm Press, Nov. 15, 1994, (3 Pages).
"Repels Mosquitos From Your Golf Course" Advertisement, Golf Course Management, 7/94 (1 Page).
"Garlic Barrier" New Products, Good Sam Highway Magazine, 5/96 (1 Page).
E. Block, "The Chemistry of Garlic and Onions," Scientific American, vol. 252 (Mar. 1985), pp. 114–119.

(List continued on next page.)

Primary Examiner—Neil S. Levy
(74) Attorney, Agent, or Firm—Blakely Sokoloff Taylor & Zafman LLP

(57) ABSTRACT

An agricultural composition of a garlic extract solution having a concentration greater than 10% by weight of a garlic extract of the garlic extract solution is disclosed. Also disclosed is an agricultural composition of a garlic extract having a concentration of greater than 10% by weight of a garlic extract and a treatment agent. So further disclosed is a method of making a garlic extract of a predetermined concentration. The method includes determining the amount of a garlic puree, separating a substantial amount of a garlic extract from the garlic puree, and adding an inert liquid to the garlic extract to form a predetermined concentration of the extract.

10 Claims, 14 Drawing Sheets

OTHER PUBLICATIONS

M.S. Venugopal & V. Narayanan, "Effects of Allitin on the Green Peach Aphid," International Pest Control (Sep./Oct. 1981), pp. 130–132.

E. Block, "The Organosuliur Chemistry of the Genus Allium–Implications for the Organic Chemistry of Sulfur," Angew. Chem. Int. Ed. Engl. (1992), pp. 1135–1178.

V. Ramakrishnan, G.J. Chintalwar & A. Banerji, "Environmental Persistence of Diallyl Disulfide, An Insecticidal Principle of Garlic and Its Metabolism in Mosquito, *Culex Pipiens Quinquifasciatus Say*," Hemosphere, vol. 18, Nos. 7–8, pp. 1525–1529 (1989).

G.G. Alln, D.I. Gustafson, R.A. Mikels, J.M. Miler & S. Neogi, "Reduction of Deer Browsing of Douglas–Fir (Pseudotsuga Menziesii) Seedlings by Quadrivalent Selenium," Elseview Science Publishers B.V. (1984), pp. 163–179.

G.A. Walters, "Compare the Effectiveness of Plant Pro–Tec (Garlic) Units with Other Methods to Prevent Browsing of Plants by Deer," Plant Pro–Tec EPA #66190–R, vol. pp. 1–4.

P.L. Tandon & B. Lal, "Comparative Efficacy of Synthetic Garlic Oil with Some Modern Insecticides Against Drosicha Mangiferae Green," Progressive Horticulture, vol. 12 (1980), pp. 61–66.

S. Deb–Kirtaniya, M.R. Ghosh, N. Adityachaudhury & A. Chatterjee, "Extracts of Garlic as Possible Source of Insecticides," Indian J. Agric. Sci. vol. 50, No. 6 (Jun. 1980), pp. 507–512.

N. Adityachaudhury, A. Bhattacharyya, A. Chowdhury & S. Pal, "Chemical Constituents of Plants Exhibiting Insecticidal, Antifeeding and Insect Growth Regulating Activities," Journal of Scientific and Industrial Research, vol. 44 (Feb. 1985), pp. 85, 99–101.

* cited by examiner

GARLIC COMPOSITION FOR FOLIAR APPLICATIONS

BACKGROUND OF THE INVENTION

1. Field of the Invention

The invention relates to a garlic formulation and more specifically to a garlic extract formulation having uses in the agricultural environment.

2. Description of Related Art

Several garlic and water-based compositions or solutions have been introduced into the marketplace as registered pesticides. These garlic/water agricultural compositions have found uses in controlling pests in the following agricultural environments: Brassica vegetables, bulb vegetables, cereal grains, citrus, cotton, cucurbit crops, forage crops, fruiting vegetables, kiwi, leafy vegetables, legume vegetables, nut trees, ornamentals, peanuts, pome fruit trees, root and tuber vegetables, small fruits and berries, and stone fruit trees. It is commonly believed that the repellent power of a garlic/water solution derives from its presence, smell, or ingestion on the crops. The treatment with garlic/water compositions offers a cost effective, environmentally-favorable pest irradication program alternative to conventional chemical pesticides.

The technical level of prior art manufacturing methods are generally incapable of measuring a percent by weight garlic extract. In general, the prior art garlic/water agricultural compositions known to the inventors utilize concentrations of approximately 10% or less by weight garlic extract. Garlic extract is the amount of solution obtained after separating the solution from substantially all of the solid particles of crushed garlic in a carrier such as ethyl alcohol or water.

Generally, the chemistry of the garlic extract is determined by the conditions of extraction. In general, there are three common extraction techniques. The harshest technique is steam distillation. The garlic is boiled and extracted from the condensed steam. Steam distillation yields diallyl disulfide as the primary garlic extract component. A second technique employs a solvent such as ethyl alcohol or other carrier at room temperature. This method yields the oxide of diallyl disulfide, called allicin, as the primary garlic extract component. Allicin is the source of the odor of garlic. A third technique employs a solvent such as ethyl alcohol at a temperature below freezing. This technique yields alliin, a molecule with optical isomerism at the sulfur and carbon atoms as the primary garlic extract component. An enzyme converts alliin into allicin. The prior garlic/water solutions known to the inventors derive their garlic extract from a pasteurized crushed garlic or puree (high temperature extraction) or room temperature extraction.

Most manufacturing methods use a straight-run, continuous, or semi-continuous methodology in which the process variables such as the density, specific gravity, and carrier content of the crushed garlic or garlic puree input material are not accurately measured. As a consequence, known manufacturing methods are incapable of accurately measuring a percent by weight of garlic extract in their final garlic extract composition.

Garlic extract compositions or solutions generally have been sold as "stand-alone" products for use in commercial agriculture as a foliar applied insect repellents, competing against other standard foliar and soil-applied pesticide and miticide products that control (kill) insects. The inventors discovered that a garlic extract in an amount of 10% or less by weight of garlic extract can be used as a synergist to increase the overall performance of other standard chemistry foliar and soil-applied products that are commercially available. For example, the inventors discovered a synergistic effect of the pesticide ENVIREPEL, manufactured by Cal Crop USA, and that carries Federal Registration No. 68826-1, a 10% garlic extract. The inventors work also included expanding the scope of products that can be synergized in the same manner to include fungicides, agricultural use anti-biotics, herbicides, defoliants, nutrients (fertilizers, plant spray aids, non-nitrogen-phosphorous-potassium (non-NPK) based materials, cytokins, kelp, humic acid, etc.) and spray adjuvants (i.e., materials that promote the wetting of a surface or spreading/penetrating properties of agricultural-use spray mixes).

The role of a garlic extract solution as a synergist developed from comprehensive field test work using a 10% by weight garlic extract solution as an insect repellent, and in combination with other pesticide products to increase combined product performance. Applications where the garlic extract solution was applied before or after the conventional chemistry treatment agent (e.g., pesticide or herbicide) did not show a measurable difference in performance of the treatment agent. However, the data showed that each time that the garlic extract solution was mixed with a treatment agent and applied at the same time, the combination of the products worked faster and was more effective than either product used alone.

What is needed is a process of making a high performance garlic extract solution containing a quantifiable amount of garlic extract that fosters the production of certain compounds and stabilizes the compounds before they are changed by enzymatic activity.

SUMMARY OF THE INVENTION

An agricultural composition of a garlic extract solution having a concentration of greater than 10% by weight garlic extract and a treatment agent. Still further disclosed is a method of making a garlic extract solution of a predetermined concentration. The method includes determining the amount of a garlic puree, separating a substantial amount of a garlic extract from the garlic puree, and adding a carrier, such as an inert liquid, to the garlic extract to form a predetermined concentration of the extract. The method of the invention identifies one key in making an effective garlic extract solution is to foster the production of certain garlic bulb derivatives and stabilize these compounds before the compounds are changed by enzymatic activity.

The invention is particularly suited to improving the efficacy, including extending the residual performance, of agricultural treatment agents including pesticides, mitacides, fungicides, herbicides, defoliants, nutritional materials, spray adjuvants commonly used in commercial agricultural. The exact mechanism that allows the garlic extract solution of the invention to alter the treatment agent's performance is not totally understood at this time. However, under the conditions defined by the invention, treatment agents that are known to be synergized by garlic extract solutions can be used to alter their chemistries to produce improved formulated treatment agents with increased field performance and increased residual activity.

The formulation of useful products of the composition of the invention or by the method of the invention are several. These include, but are not limited to, the formulation of garlic extract solutions with another product in a mixing tank to produce a new product that would be packaged in a single container; formulation of a garlic extract solution with another product(s) in a container or tank that would eventually be applied to an application site; and formulation of a garlic extract solution with another product(s) in a container that would eventually be diluted and applied to an application site.

Additional features and benefits of the invention will become apparent from the detailed description, figures, and claims set forth below.

DETAILED DESCRIPTION OF THE INVENTION

The invention relates to an agricultural composition having a garlic extract solution containing garlic extract in a concentration greater than 10% by weight of the solution. The invention also relates to an agricultural composition having a garlic extract solution with a concentration of garlic extract of greater than 10% by weight and a treatment agent.

The invention further relates to a method of making a garlic extract solution of a predetermined concentration. Unlike known prior art methods of formulation, the methodology of the invention utilizes controlled batch processing that allows the accurate determination of the percent by weight of garlic extract in the garlic solution as well as any other component ingredients that are contemplated for the finished product. In this manner, consistently accurate garlic extract solutions can be produced that allow for much higher and chemically stable garlic extract concentrations to be formulated.

Explanations of how garlic extract or a garlic extract composition can be an effective synergist are product chemistry specific. The formation of organo-sulfur compounds appears to be essential to the product's ability to be an effective synergist. These compounds and their purported purpose include the following: Allitin (insect growth regulator or IGR activity, feeding depressant, ova-positioning reduction effect), allicin (antimicrobial, growth inhibiting effect on gram-neg/pos bacteria), diallyl disulfide (interacts with nitrites, repels vertebrates/insects), diallyl trisulfide (anti-viral, fungicide properties), $SO_3H$ (interacts with plant metabolic functions and has anti-bacterial performance), hydroxide ion (produced by enzymatic activity and available for bonding with other non-organic compounds), COO– (produced by enzymatic activity and available for bonding with other non-organic compounds), COOH, $CH_2$, $CH_3$, dimethyl sulfoxide (DMSO) (provides translocation/penetration properties in both leaf tissue and insect tissue). Thus, the method of obtaining the garlic extract solution and the components of that solution appear to be important.

The organo-sulfur compounds mentioned are difficult to identify by course analysis. Allitin and allicin are bi-products of enzymatic reactions that begin when the garlic bulb is first cut or crushed and are time dependent. Other bi-products of the enzymatic activity are the diallyl-compounds that are extremely reactive and if not stabilized change forms into other organo-sulfur compounds.

Figure 1:
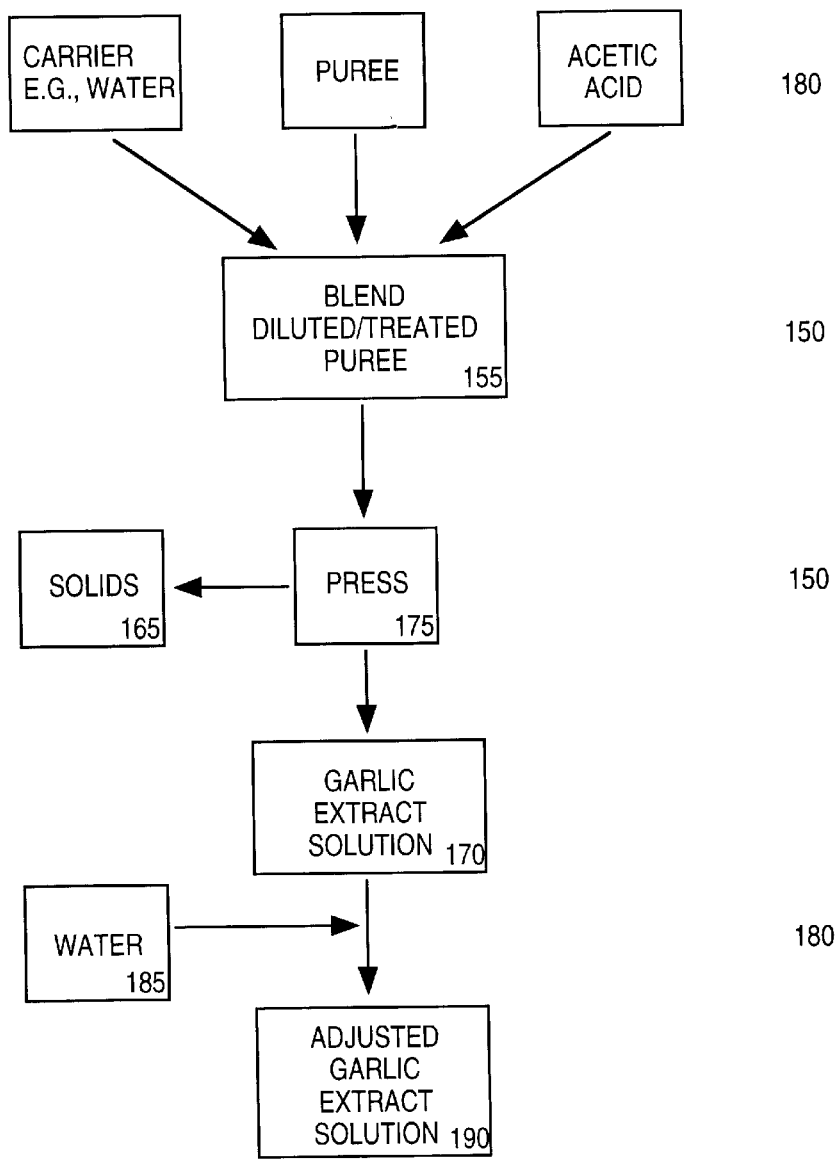
FIG. 1 is a flow chart of the method steps of an embodiment of the invention.

FIG. 1 illustrates a flow chart of a batch processing method contemplated by the invention. In one embodiment, a batch process starts with raw materials of 100% garlic puree, a carrier such as, for example, water, and acetic acid. The garlic has been pureed and frozen at temperatures of 32° F. (0° C.) or less, and preferably stored at least six months in this frozen state. The inventors believe that extracting garlic extract that had previously been frozen increases the amount of organo-sulfur compounds that make a garlic extract solution an effective synergist. The inventors' method is in contrast to prior art methods that extracted the garlic extract at room temperature using garlic stored at room temperature or extraction methods at high temperature. In this manner, the method of the invention fosters the production of desired garlic bulb derivatives before the derivatives are changed by enzymatic activity. It is to be appreciated, however, that the general method of the invention and the product produced in accordance with that method could be practiced with crushed garlic or garlic puree formed at room temperature or high temperature although the results of the product would be expected to be inferior to the methodology based on frozen garlic.

The pureed garlic is thawed prior to use. In this embodiment of the method of the invention, raw materials of a carrier, such as dechlorinated water (pH of approximately 5.0) and a preservative such as glacial acetic acid are also added in the batch process. It is to be appreciated that a variety of carriers may be used, including both inert and non-inert carriers. The acetic acid acts as a preservative by arresting fermentation. The acetic acid may also act as a leaching agent.

The thawed garlic puree, water, and acetic acid are each accurately weighed and placed in a blending tank in desired amounts for a blending step 150. The amount of water/acetic acid added determines the final concentration of the extract solution. A 100% extract solution, for example, would have no water (and/or acetic acid) added. The materials are blended to a substantially homogeneous state 155 and then subjected to a filtering step 160, by being pumped, for example, into a mechanical, hydraulic, or pneumatic press 175. In press 175, a garlic extract solution 170 is substantially separated from the garlic puree solids 165. In one embodiment, the press consists of a plunger capable of applying between 1 to 1,000 lb/in$^2$ (PSI) pressure to the garlic puree blend. The garlic puree blend is placed beneath the plunger and over a screen sufficient to produce a maximum particulate size of 200 microns in garlic extract solution 170.

After filtering step 160, garlic extract solution 170 is weighed to determine the amount of garlic extract in the solution. Garlic extract solution 170 is then placed in a storage tank and the concentration of garlic extract adjusted with the addition of a carrier such as dechlorinated water 185 in a concentration adjusting step 180. Adjusting step 180 yields a garlic extract solution 190 having an accurately determined concentration of garlic extract. Once again, it is to be appreciated that a variety of carries may be used, including inert and non-inert carriers.

EXAMPLE 1

The following example is illustrative of the formulation process described above.

82 lbs of thawed garlic puree is placed in a container with 4 lbs glacial acetic acid and 66 lbs of water. The components are mixed, then put into a filter press. The filter press separates 38.5 lbs of garlic puree solids and 104 lbs of garlic extract solution. The difference between the amount of garlic puree into the press and the garlic puree solids out of the press is equivalent to the amount of garlic extract in the garlic extract solution. In this example, 43.5 lbs garlic extract, or a garlic concentration of 41.8% (43.5 lbs/104 lbs×100). The garlic extract solution may be diluted with water or another inert to dilute the concentration of garlic extract from 41.8% to another desirous concentration.

Figure 2:
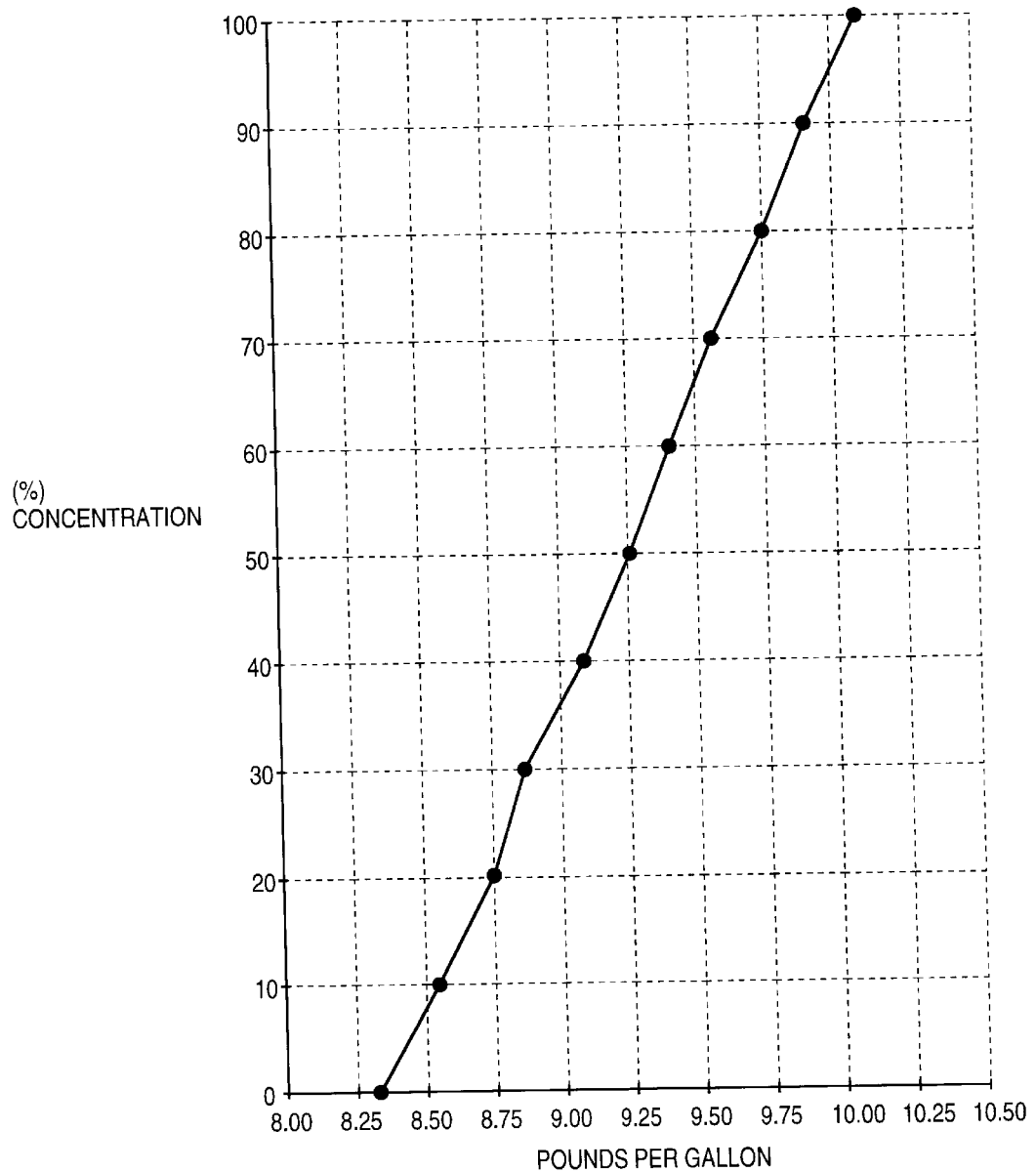
FIG. 2 is a graphical representation of the product weight per gallon versus percent by weight garlic extract.
Figure 3:
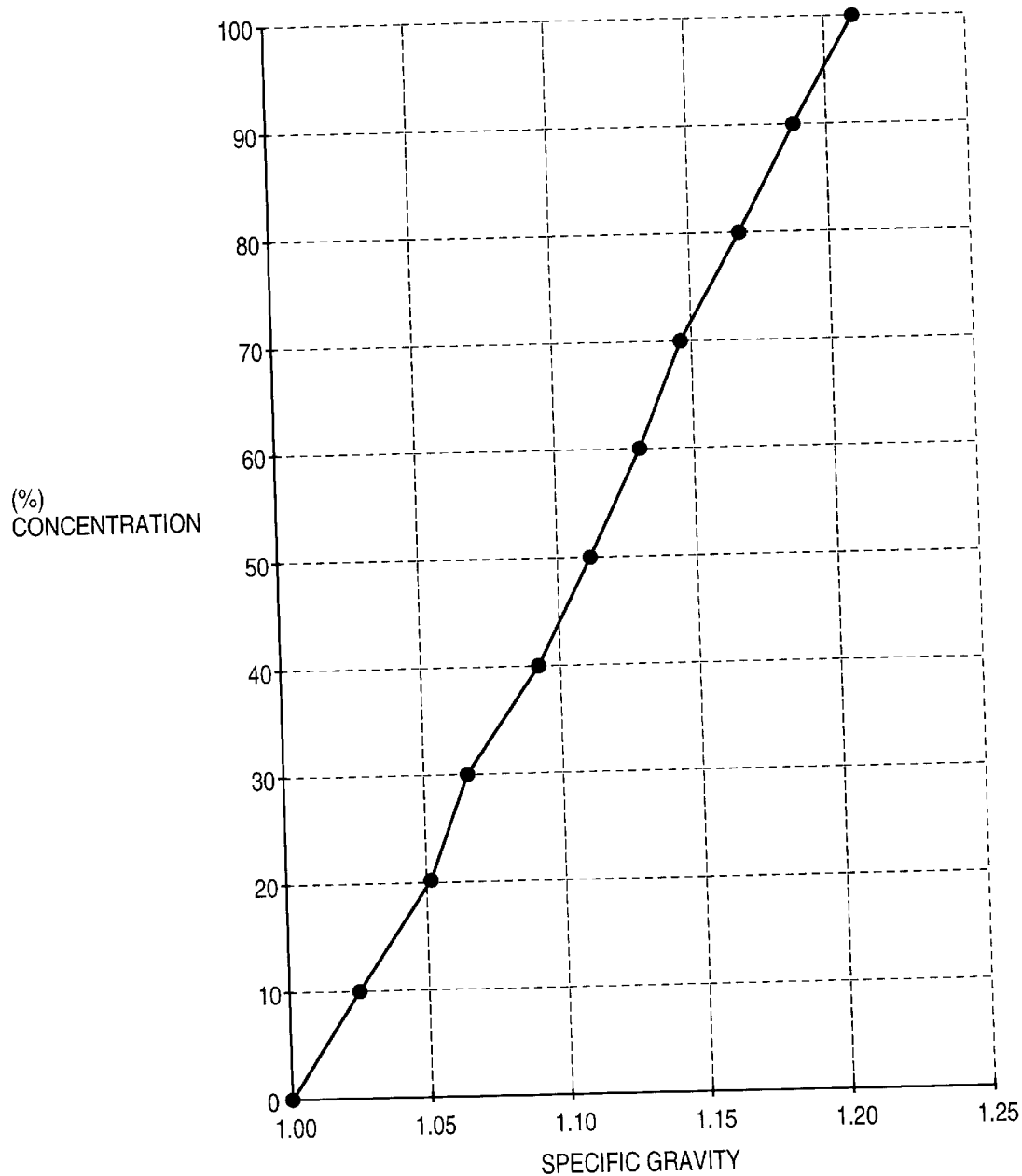
FIG. 3 is a graphical representation of the specific gravity versus percent by weight garlic extract.

FIG. 2 is a graphical representation of a product weight per gallon versus percent garlic extract in a garlic extract solution that is used to determine the percent garlic extract available in a garlic extract solution prepared by the process of the invention, for formulation. FIG. 3 is a graphical representation of the specific gravity of various concentrations of garlic extract prepared by the process of the invention.

The garlic extract solution of the invention may be used alone or as a synergist with other treatment agents as an agricultural composition. As a synergist, the garlic extract solution of the invention can aid standard chemistry products including, but not limited to, pesticides, miticides, fungicides, agricultural use anti-biotics, herbicides, defoliants, water, nutrients, and spray adjuvants to produce higher performing formulated products.

As a synergist, the garlic extract solution of the invention can be packaged in a single container with a treatment agent and sold as a combined commercial product. Alternatively, the garlic extract solution of the invention may be combined together with or added separately later to a treatment agent as a product that is to be diluted prior to application.

Agents for agricultural use including pesticides, herbicides, fungicides, anti-biotics, etc., generally require Environmental Protection Agency (EPA) registration at the federal level and often require state registration prior to sale or use. These federal and state agencies generally register a product based on an analysis of the safety of a sample of the product. The commercial product generally contains a specified amount of the active chemical or chemicals of the agent and a portion of inert substances, such as water. Once a product is registered, the manufacturer is not permitted to change the amount of active agent (e.g., active chemical or chemicals) and offer a new product for sale without first seeking registration of the EPA for their new product.

Most conventional treatment agents have levels of active agent(s) ranging from 0.1% by weight to 95% by weight. The remainder of the treatment agent is typically comprised of inerts, commonly water. The garlic extract solution of the invention can be classified by the EPA as an inert or an active depending on how it is used. Accordingly, the garlic extract solution of the invention can replace inerts and aid the treatment agent in a synergistic fashion without requiring additional EPA registration for the treatment agent. Thus, the agricultural composition of the invention will replace an inactive inert such as water with the proactive inert garlic extract solution of the invention to produce a higher performing treatment agent/garlic extract solution agricultural composition.

Alternatively, other treatment agents registered by the EPA are solely an active agent (e.g., 100% active chemical or chemicals). These "pure" treatment agents are registered by the EPA for use based on a specified amount of active ingredient for an area of application, e.g., pounds per acre. The "pure" treatment agents are provided in "pure" form to be diluted with inerts (generally water) and applied to an area. Accordingly, the garlic extract solution of the invention can replace a portion of the dilutant and aid the "pure" treatment agent in a synergistic fashion in compliance with EPA requirements for use of the "pure" treatment agents over a specified area. The process can be used to add concentrations from 10% to 100% of garlic extracts. The concentrations shown in FIG. 2 can be produced from the process of the invention.

To be effective, an agricultural composition of garlic extract solution and treatment agent(s) requires an effective minimum amount of garlic extract, such as for example, 10% by weight concentration of garlic extract in the combined composition. Thus, when replacing an inert in a treatment agent, consideration must be given to maintaining the registered concentration of the treatment agent as well as an effective minimum concentration of garlic extract. Prior art garlic extract solutions of less than or equal to 10% by weight concentration of garlic extract could not be utilized as an inert replacement because such solutions could not satisfy either criteria. The garlic extract solution and method of the invention can be used to replace inerts in EPA-registered treatment agents because the method produces an accurate, quantifiable, greater than 10% by weight concentration of garlic extract.

Figure 4A:
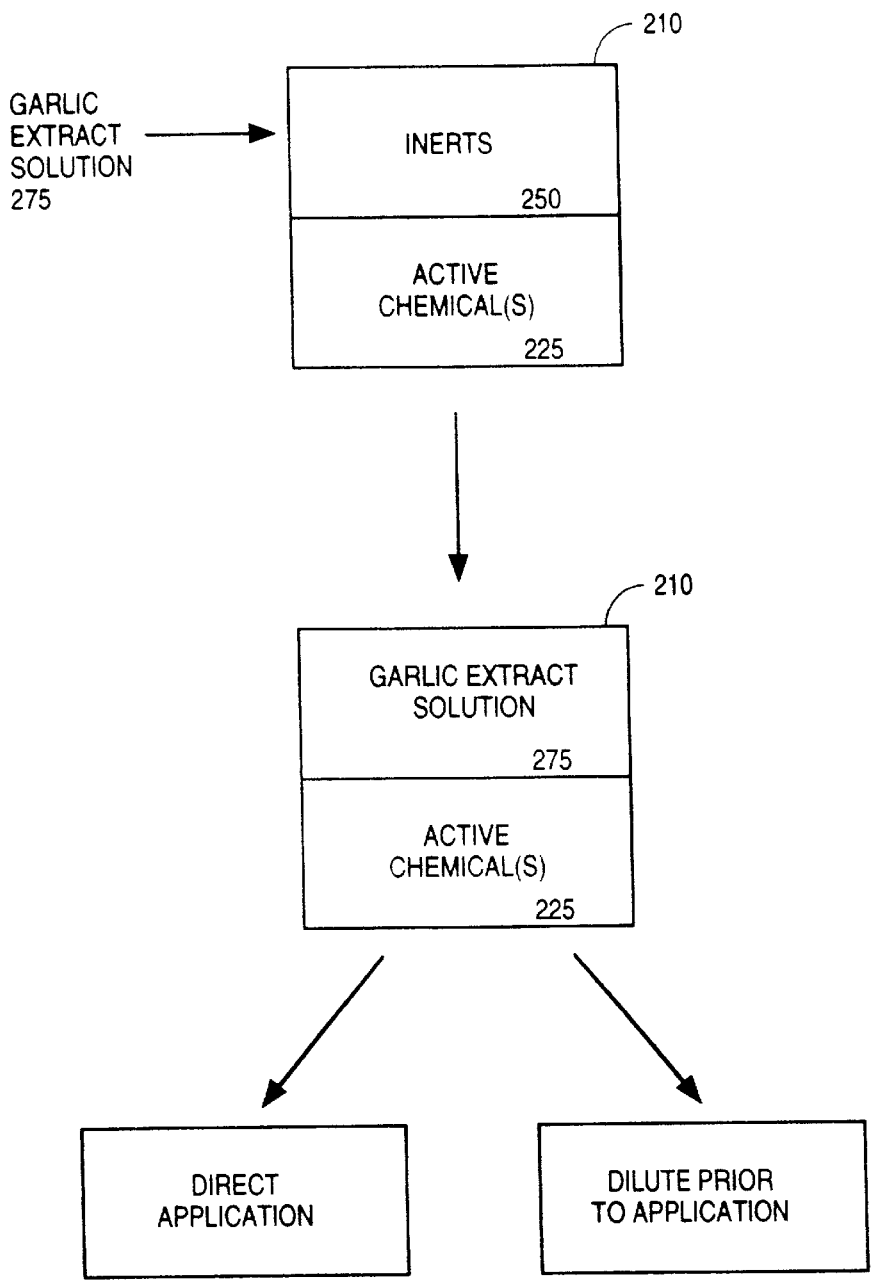
FIG. 4a illustrates the replacement of inerts in an EPA-approved treatment agent with the garlic extract solution of the invention.

FIG. 4a illustrates the method of replacement of the inert portion of an EPA-registered commercially available agricultural agent 210. In FIG. 4a, agent 210 includes an amount 225 of active chemical(s) 225 and inerts 250. According to the invention, since garlic extract solution 275 is classified as an inert, garlic extract solution 275 may replace inerts 250 in an EPA-registered commercially available product 210 as illustrated. Thus, the invention contemplates that the proactive garlic extract solution 275 can be added to an EPA-registered product 210 to produce a higher performing treatment agent agricultural composition without the need for additional EPA registration. Two uses of the agricultural composition include, but are not limited to, direct application to agriculture sites, such as a garden or crop, or further dilution with, for example, water prior to application.

Figure 4B:
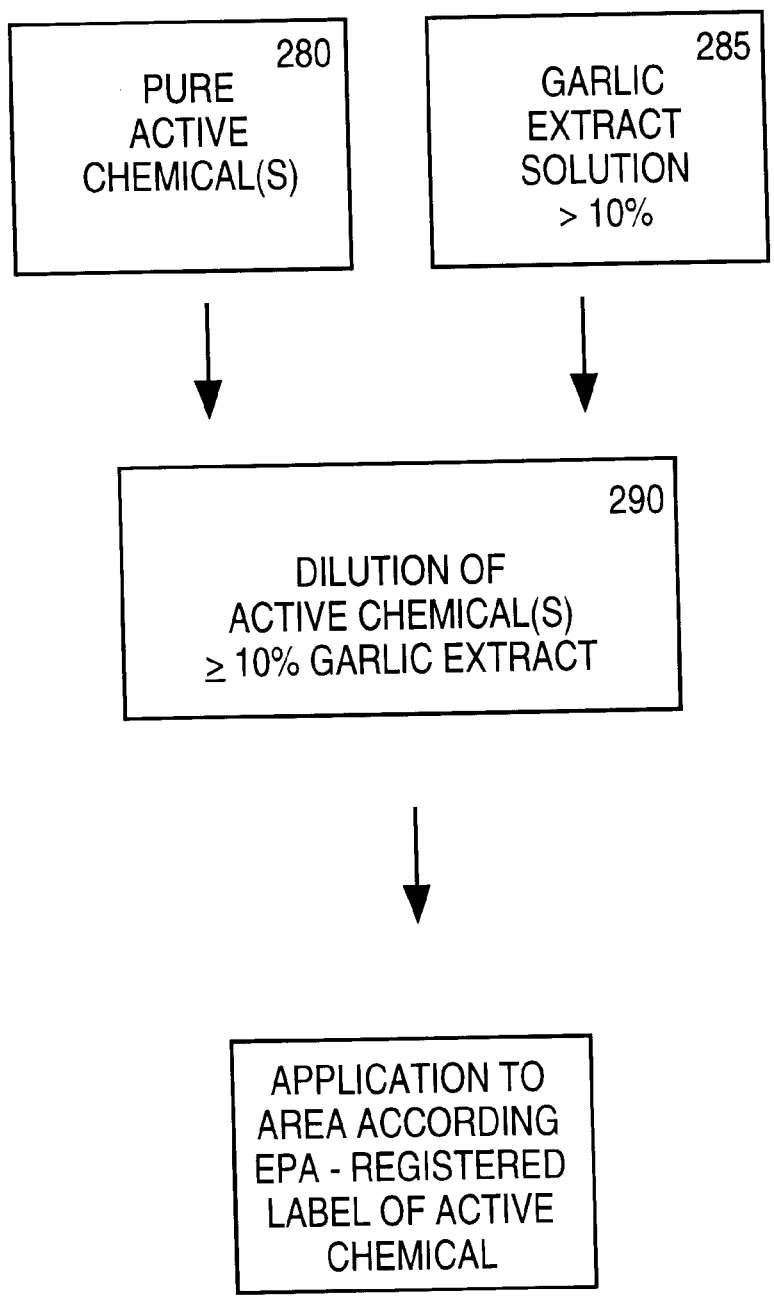
FIG. 4b illustrates the dilution of an EPA-approved treatment agent with the garlic extract solution of the invention.

FIG. 4b illustrates a second situation where a treatment agent 280 is supplied by a manufacturer in "pure" form, e.g., 100% active chemical or chemicals. According to its EPA registration, a specified amount of treatment agent 280 may be used for an area of application of, for example, certain pounds per acre. Accordingly, prior to use, treatment agent 280 is diluted with inerts (such as water). FIG. 4b shows the step 290 of adding treatment agent 280 to a mixing tank and diluting treatment agent 280 with a concentrated garlic extract solution 285. In this manner, the concentrated garlic extract solution 285 is such that upon its dilution with treatment agent 280 (and possibly other inerts), the diluted solution will contain a prescribed amount of garlic extract, preferably 10% by weight or greater of the diluted mixture. In the case of the prescribed 10% garlic extract solution, it is to be appreciated that such a final solution would not be possible unless a garlic extract solution having a greater weight percent garlic was used. Further, treatment agent 280 will be diluted to its appropriate concentration for area application. Thus, step 295 illustrates the application of treatment agent 280 to an area pursuant to EPA registration.

To determine the weight percent of the garlic extract solution necessary to yield a finished agricultural composition (i.e., garlic extract solution plus treatment agent(s)) having a minimum of 10% by weight concentration of garlic extract, the following formula is used:

Finished formulated product % by weight [garlic extract, treatment agent, inerts]=[(treatment agent) (respective active and inert by weight concentrations)+(garlic extract active and inert by weight concentrations)]/(gallons formulated).

EXAMPLE 2

The following example utilizes the above equation for combining a 40% garlic extract solution with LANNATE LV™, a pesticide manufactured by E. I. DuPont De Nemoirs Co. of Wilmington, Del., to formulate an agricultural composition having a garlic extract amount by weight of 10% and maintain the maximum concentration of Lannate LV possible of 29% by weight active and with a product weight of 8.27 pounds per gallon.

10% by weight garlic+A% by weight Lannate LV+B% by weight inerts=[((9.1 lbs per gallon)(40% active)+(9.1 lbs/gallon)(60% inert))('C' gal)+((8.27 lbs/gal)(29% active)+(8.27 lbs/gal)(71% inerts)('D' gal))]/('C' gal+'D' gal)= [((3.64 lbs/gal active)+(5.46 lbs/gal inert))('C' gal)+((2.4 lbs/gal active)+(5.87 lbs/gal inerts))('D' gal))]/('C'+'D' gal).

Solving by iteration to produce one gallon of formulated product of an agricultural composition (i.e., 'C'+'B'=1.0) yields:
'A'=21.69%, 'B'=69.21%, 'C'=0.235 gal, 'D'=0.765 gal
This relationship yields the following:

(0.855 lbs garlic active)+(1.283 lbs garlic inerts)+(1.836 lbs active Lannate LV)+(4.49 lbs inert Lannate LV)=[(0.855 lbs garlic active)+(1.836 lbs active Lannate LV)+(5.773 lbs inerts)=10% by weight garlic extracts+21.69% by weight Lannate active+ 68.21% inerts.

EXAMPLE 3

The following example describes the formulation of a garlic extract solution and a carbamate pesticide/insecticide carbaryl. To formulate a 10% by weight garlic extract solution, 5% by weight carbaryl active product, using a 40% by weight garlic extract solution and 100% by weight active carbaryl is as follows:

10%G active+5%C active+85% Inerts=X(Carbaryl 100%)+Y(Garlic 40%)+Z(Inerts)

(10.27 lb/gal)(9.1 lb/gal)(8.33 lb/gal) (10.27 lb active/gal) (3.64 lb active/gal)(8.33 lb inert/gal)
Solving by iteration on a per gallon basis yields:

(0.86 lbs active)+(0.43 lbs active)+(7.31 lbs inerts)=(0.43 lbs C)+(2.15 lbs G 40%)+(6.02 lbs I)

Formulated product weight is 8.6 lbs/gallon. The per gallon breakdown for formulation is as follows:
X=5.36 ounces (0.041875 gal) Carbaryl concentrate
Y=30.24 ounces (0.23625 gal) Garlic 40% concentrate
Z=92.4 ounces (0.72187 gal) water The above formulation demonstrates formulating garlic extract solution into other products. The pounds active treatment agent per acre applied label requirements of the EPA-registered treatment agent is followed with the exception that garlic extract solution replaces some or all of the inert portions of the treatment agent. This avoids re-registration of the treatment agent.

FIGS. 5–11 illustrate the synergistic effects of the garlic extract solution of the invention with commercially available treatment agents. In each example, a minimum of 10% by weight concentration of garlic extract was combined with the individual treatment agents and the results studied.

Figure 5:
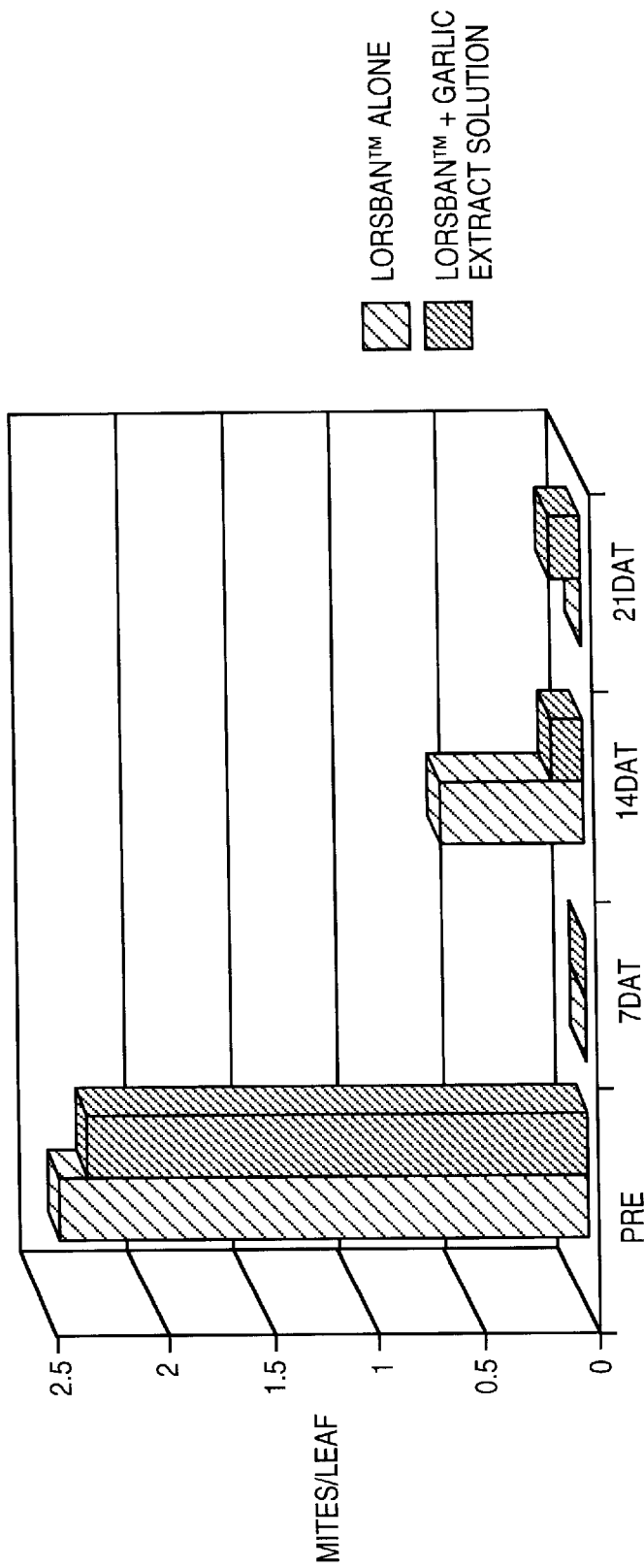
FIG. 5 illustrates the performance of an organo-phosphate based pesticide and an organo-phosphate-based pesticide combined with the garlic extract solution of the invention to treat mites.

FIG. 5 compares the performance of the organophosphate-based pesticide LORSBAN™, manufactured by Dow Elanco and a LORSBAN™/garlic extract solution combination FIG. 5 illustrates the improvement in performance for the combination for treatment of mites. The increase in performance is measured by the increased kill and extended residual performance of the pesticide versus the pesticide combined with a garlic extract solution of the invention.

Figure 6:
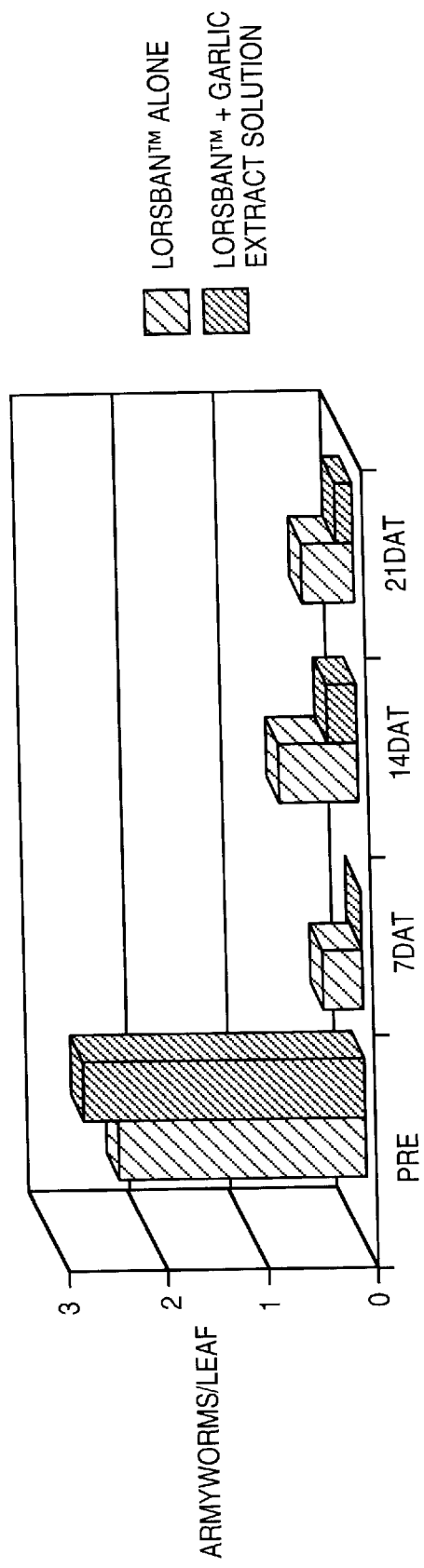
FIG. 6 illustrates the performance of an organo-phosphate-based pesticide and an organo-phosphate-based pesticide combined with the garlic extract solution of the invention to treat armyworms.

FIG. 6 compares the performance of the organophosphate pesticide LORSBAN™ and a LORSBAN™/garlic extract solution combination. FIG. 6 illustrates the improvement in performance for the combination for treatment of armyworms. The increase in performance is measured by the increased kill and extended residual performance of the pesticide versus the pesticide combined with a garlic extract solution of the invention.

Figure 7:
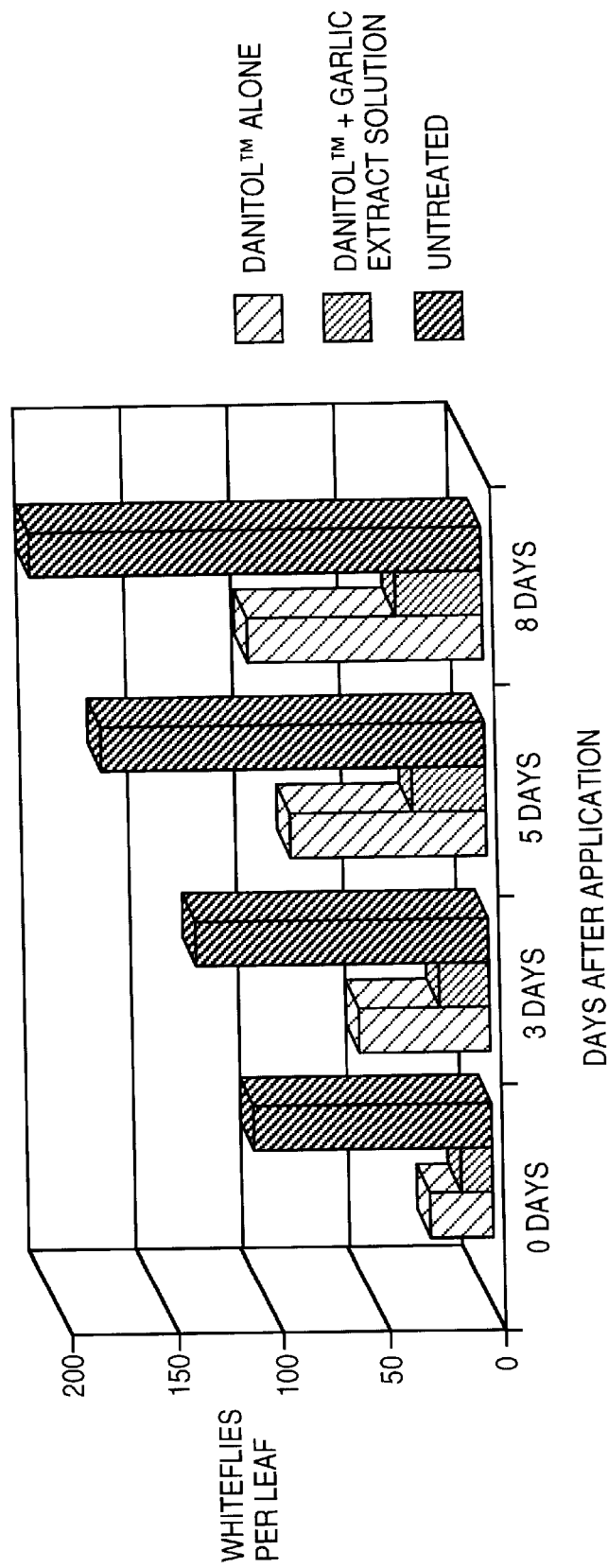
FIG. 7 illustrates the performance of a pyrethroid-based pesticide and a pyrethroid-based pesticide combined with the garlic extract solution of the invention to treat whiteflies.

FIG. 7 compares the performance of the pyrethroid-based pesticide DANITOL™, manufactured by Valent USA and a DANITOL™/garlic extract solution combination. FIG. 7 illustrates the improvement in performance for the combination for the treatment of whiteflies. The increase in performance is measured by the increased kill and extended residual performance of the pesticide versus the pesticide combined with a garlic extract solution of the invention.

Figure 8:
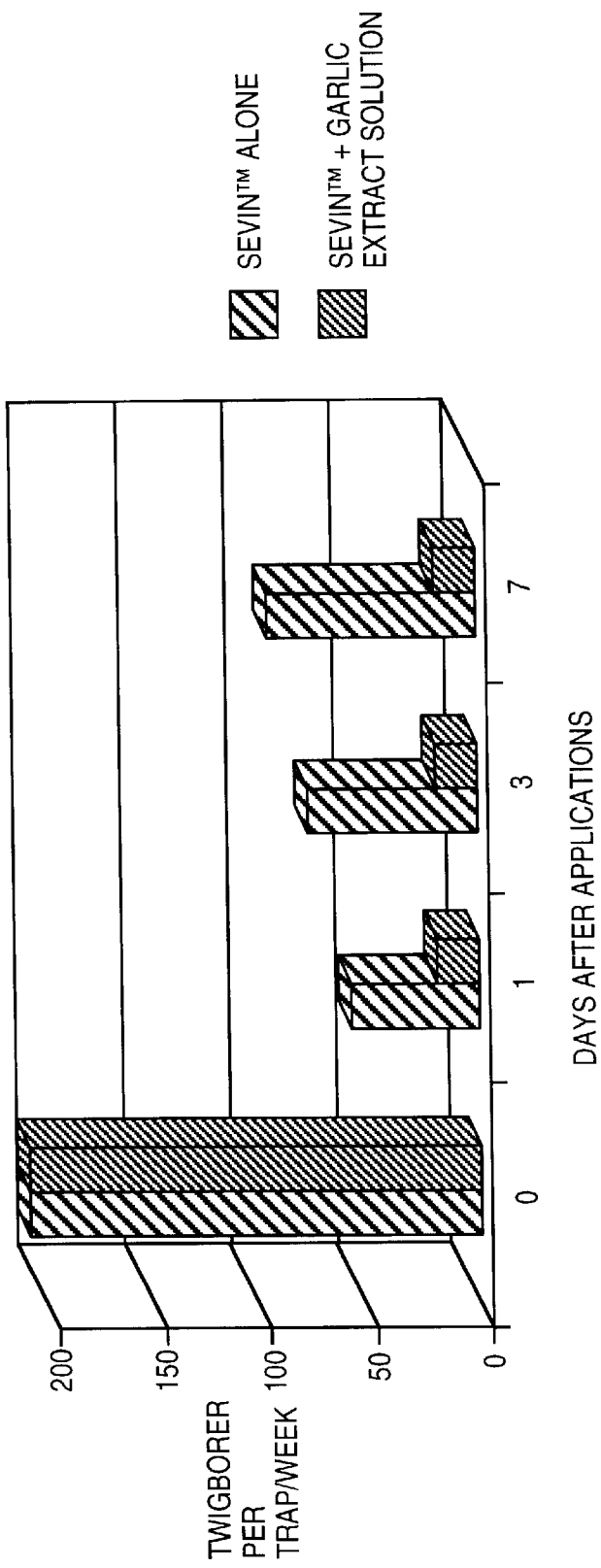
FIG. 8 illustrates the performance of a carbamate-based pesticide and a carbamate-based pesticide combined with the garlic extract solution of the invention to treat twigborers.

FIG. 8 compares the performance of the carbamate-based pesticide SEVIN, manufactured by Union Carbide Corporation of New York, N.Y., and a SEVIN™/garlic extract composition combination. FIG. 8 illustrates the improvement in performance for the combination for treatment of twigborers. The increase in performance is measured by the increased kill and extended residual performance of the pesticide versus the pesticide combined with a garlic extract solution of the invention.

Figure 9A:
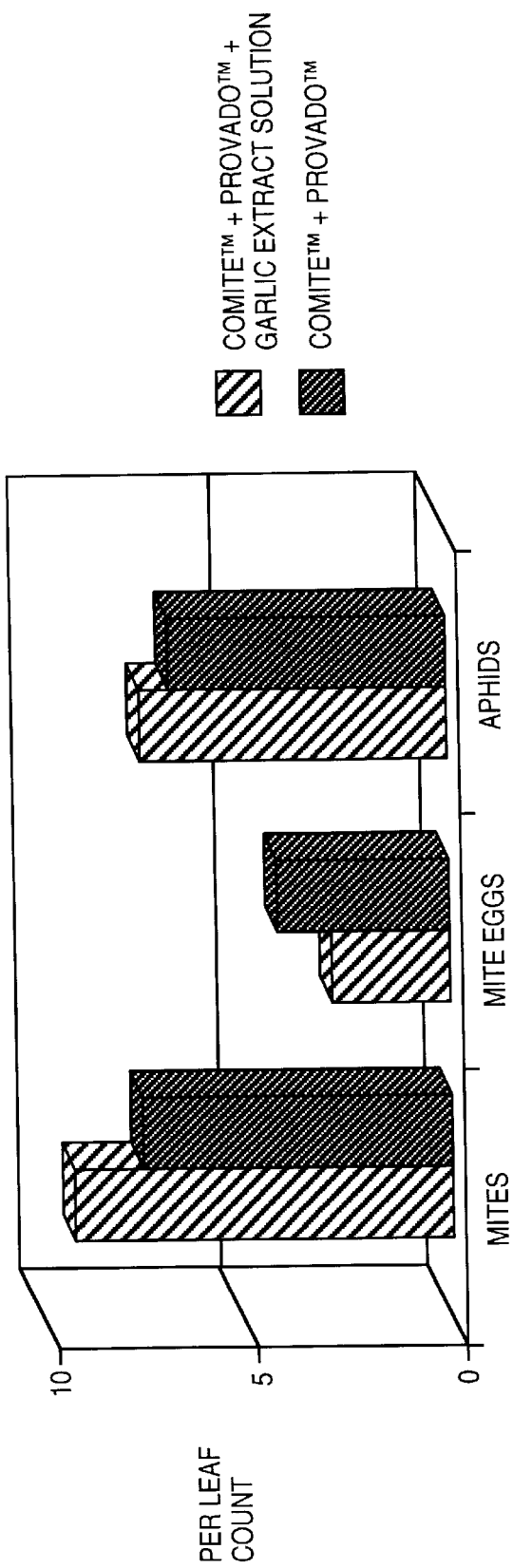
FIG. 9a illustrates the performance for pretreatment of cotton with a miticide and an aphicide and miticide and an aphicide combined with the garlic extract solution of the invention.

FIG. 9a compares the performance for pretreatment of cotton with a mitice, COMITE™ (manufactured by Uniroyal Chemical, Naugatuck, Conn.) and aphicide PRO- VADO™ (manufactured by Bayer) and a COMITE™/PROVADO™/garlic extract solution combination. For the pre-treatment of mites and aphids, the per leaf count of COMITE™/PROVADO™ and COMITE™/PROVADO™/garlic extract solution is similar with the COMITE™/PROVADO™ treatment having slightly better results. With respect to mite eggs, however, the COMITE™/PROVADO™/garlic extract solution shows better results than the COMITE™/PROVADO™ used alone.

Figure 9B:
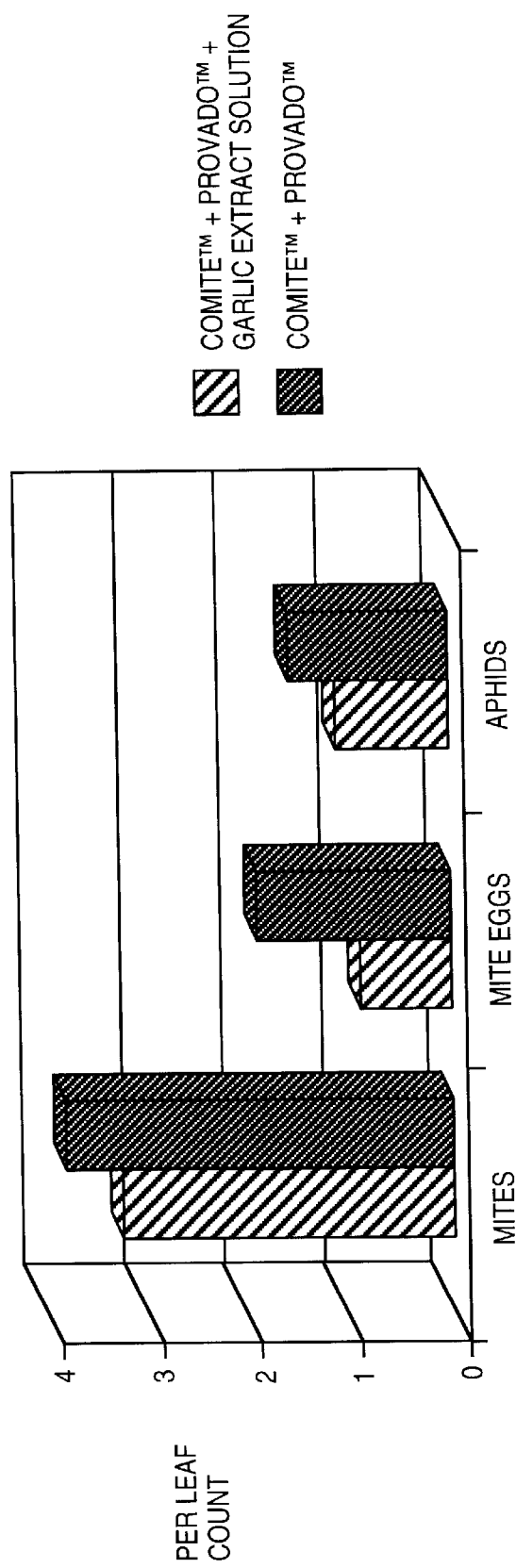
FIG. 9b illustrates the performance of the miticide and aphicide and miticide and aphicide combined with garlic extract of FIG. 9a after 7 days.
Figure 9C:
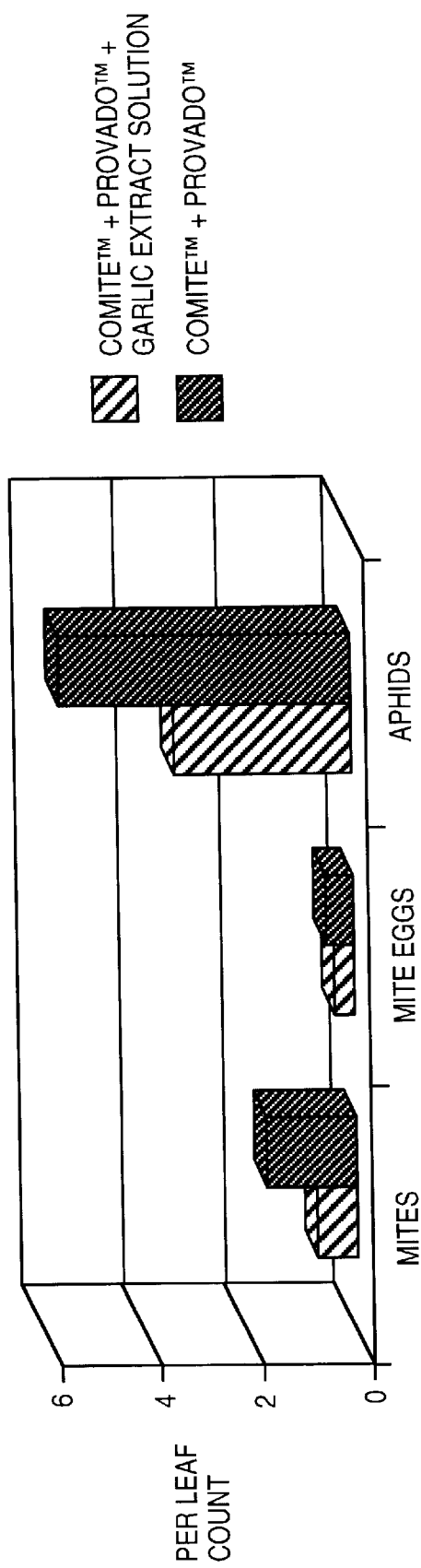
FIG. 9c illustrates the performance of the miticide and aphicide and miticide and aphicide combined with garlic extract of FIG. 9a after 21 days.

FIG. 9b compares the performance of COMITE™/PROVADO™ and COMITE™/PROVADO™/garlic extract solution after seven days. FIG. 9b shows a marked improvement in performance of the miticide/aphicide combined with the garlic extract solution of the invention for mites, mite eggs, and aphids. FIG. 9b shows significantly better performance of the combination after 21 days.

Figure 10:
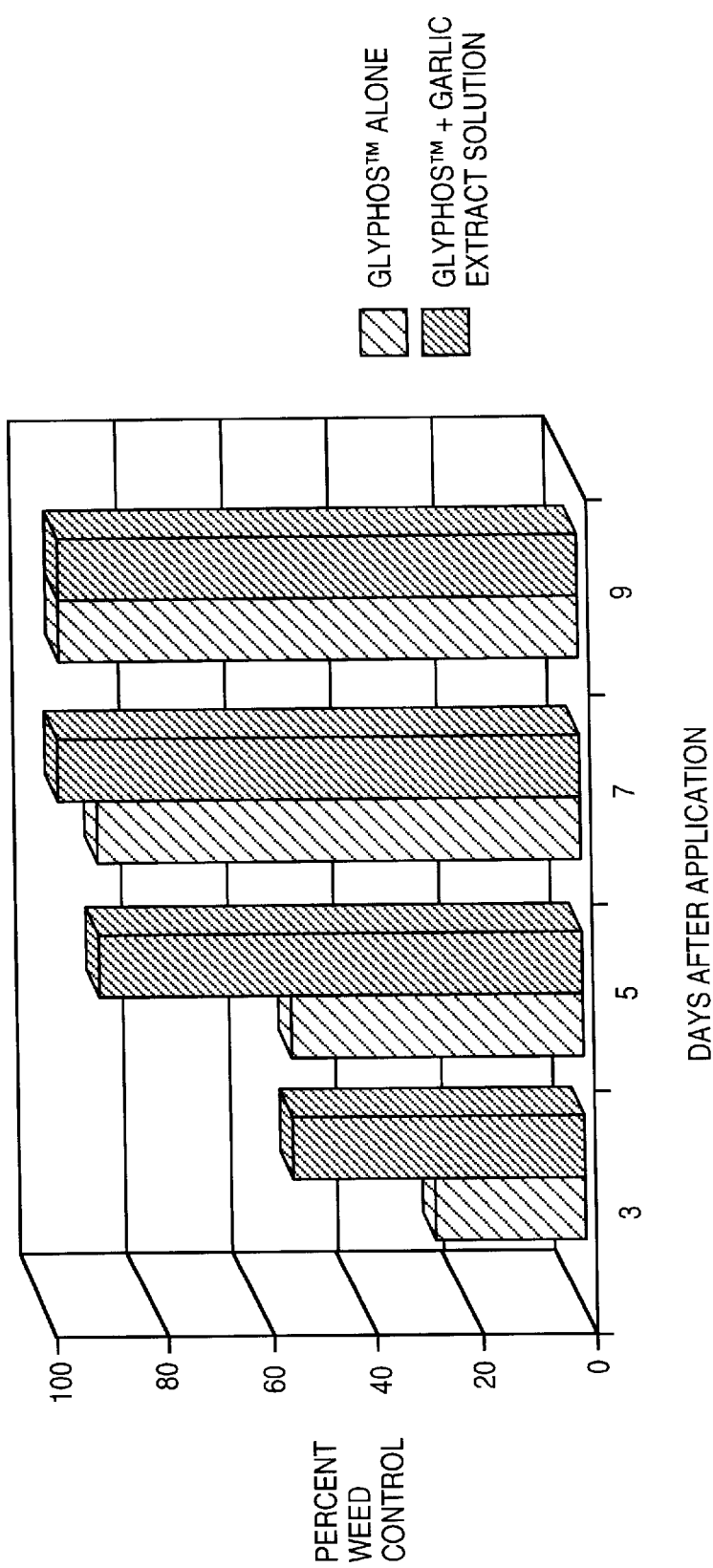
FIG. 10 illustrates the performance of a non-systemic contact herbicide and a non-systemic contact herbicide combined with the garlic extract solution of the invention to treat weeds.

FIG. 10 compares the performance of a non-systemic contact herbicide GLYPHOSATE and a GLYPHOSATE garlic extract solution combination. FIG. 5 illustrates the improvement in performance for weed control.

Figure 11:
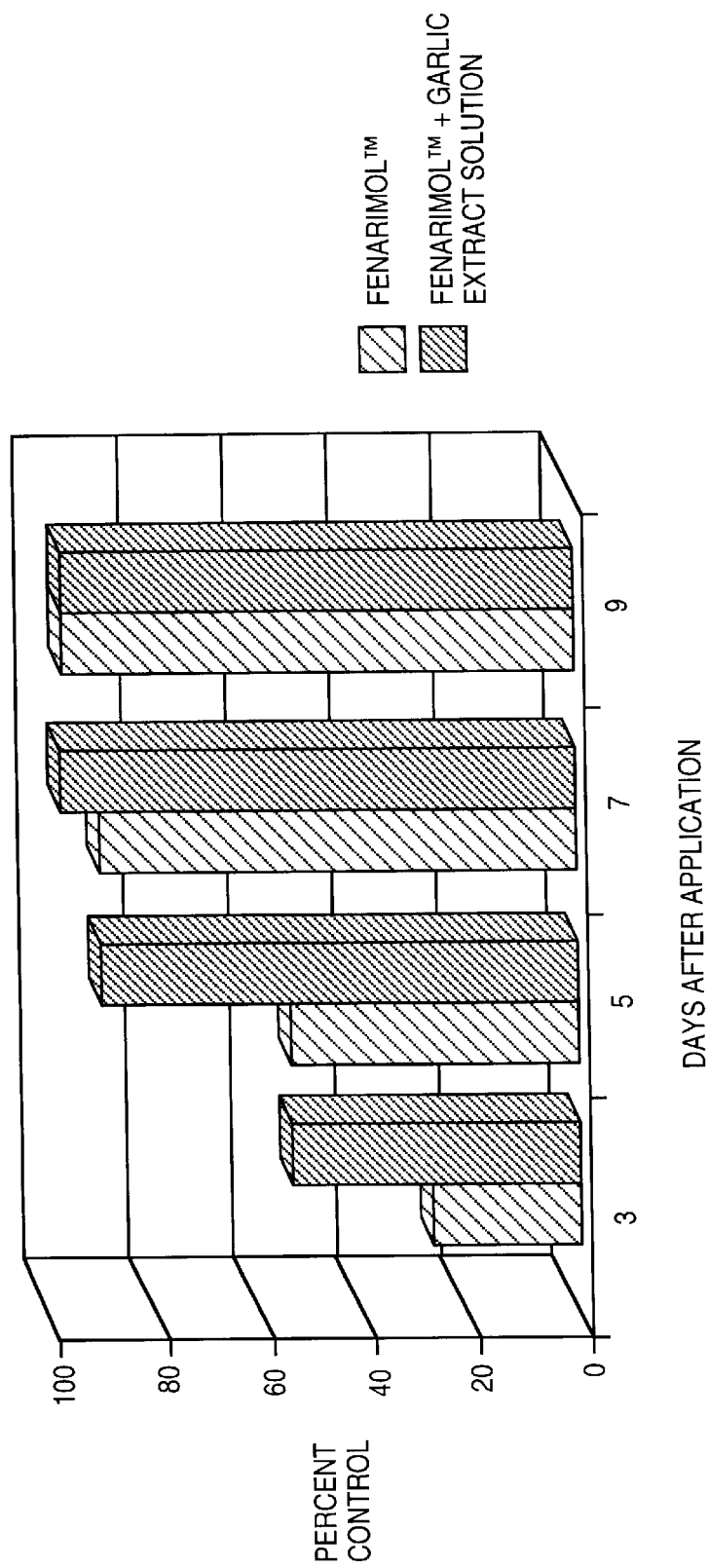
FIG. 11 illustrates the performance of a systemic fungicide and a systemic fungicide combined with the garlic extract solution of the invention.

FIG. 11 compares the performance of a systemic fungicide, RUBIGAN™, manufactured by Dow Elanco, and a RUBIGAN™/garlic extract solution combination. FIG. 5 illustrates the improvement in performance for the combination in terms of days after application.

In the preceding detailed description, the invention is described with reference to specific embodiments thereof. It will, however, be evident that various modifications and changes may be made thereto without departing from the broader spirit and scope of the invention as set forth in the claims. The specification and drawings are, accordingly, to be regarded in an illustrative rather than a restrictive sense.

What is claimed is:

1. An agricultural composition comprising:
    a first component comprising a garlic extract solution having a quantifiable concentration of greater than ten percent by weight of a garlic extract, the garlic extract comprising allitin, allicin, diallyl disulfide, and dimethyl sulfoxide; and
    a second component comprising an agricultural treatment agent of one of a pesticide, miticide, fungicide, anti-biotic, herbicide, defoliant, nutrient, adjuvant, and water.

2. The agricultural composition of claim 1, wherein the garlic extract has a maximum particulate size of 200 microns.

3. A method of formulating a treatment agent for application to a crop, the method comprising:
    providing a treatment agent including a garlic extract solution of greater than 10 percent by weight of a garlic extract, the garlic extract comprising allitin, allicin, diallyl disulfide, and dimethyl sulfoxide and one of a pesticide, miticide, fungicide, anti-biotic, herbicide, defoliant, nutrient, adjuvant, and water; and
    diluting the treatment agent with a diluting solution to a predetermined concentration suitable for a foliar application.

4. An agricultural composition comprising a garlic extract solution having a concentration greater than ten percent by weight of a garlic extract, the garlic extract solution made by the process of:
    separating a portion of a garlic extract from an amount of the garlic puree, the garlic extract comprising active ingredients of allitin, allicin, diallyl disulfide, and dimethyl sulfoxide; and
    adding an inert liquid to the garlic extract to form a composition having a concentration greater than ten percent by weight of the garlic extract.

5. The composition of claim 4, wherein the garlic puree is held at a temperature of 32° F. (0° C.) or less until the separation.

6. An agricultural composition formed without using ethyl alcohol comprising:
    a first component comprising a garlic extract solution having a concentration greater than ten percent by weight of a garlic extract, the garlic extract comprising allitin, allicin, diallyl, disulfide, and dimethyl sulfoxide; and
    a second different component comprising a pesticide.

7. A method of formulating a treatment agent for application to a crop, the method comprising:
    providing a treatment agent including a garlic extract solution having a concentration greater than ten percent by weight of the garlic extract, the garlic extract comprising allitin, allicin, diallyl disulfide, and dimethyl sulfoxide and one of a pesticide, miticide, fungicide, anti-biotic, herbicide, defoliant, nutrient, and adjuvant; and
    diluting the treatment agent with an inert compound.

8. A method of formulating a treatment agent for application to vegetation, the method comprising:
    providing a treatment agent including a first component comprising a garlic extract solution having a concentration greater than ten percent by weight of the garlic extract, the garlic extract consisting essentially of allitin, allicin, diallyl disulfide, and dimethyl sulfoxide and a second component comprising one of a pesticide, miticide, fungicide, anti-biotic, herbicide, defoliant, nutrient, and adjuvant; and
    diluting the treatment agent with an inert compound wherein the garlic puree is held at a temperature of 32° F. (0° C.) or less until the separation.

9. An agricultural composition comprising:
    a first component consisting of a garlic extract solution having a quantifiable concentration of greater than ten percent by weight of a garlic extract, the garlic extract consisting of allitin, allicin, diallyl disulfide, and dimethyl sulfoxide; and
    a second component consisting of an agricultural treatment agent of one of a pesticide, miticide, fungicide, anti-biotic, herbicide, defoliant, nutrient, adjuvant, and water.

10. An agricultural composition comprising:
    a first component consisting essentially of a garlic extract solution having a quantifiable concentration of greater than ten percent by weight of a garlic extract, the garlic extract consisting essentially of allitin, allicin, diallyl disulfide, and dimethyl sulfoxide; and
    a second consisting essentially of an agricultural treatment agent of one of a pesticide, miticide, fungicide, anti-biotic, herbicide, defoliant, nutrient, adjuvant, and water.

* * * * *